United States Patent [19]

Dai

[11] Patent Number: 4,642,342
[45] Date of Patent: Feb. 10, 1987

[54] AZETIDINEDIONE URETHANES

[75] Inventor: Shenghong A. Dai, Wallingford, Conn.

[73] Assignee: The Dow Chemical Company, Midland, Mich.

[21] Appl. No.: 811,854

[22] Filed: Dec. 20, 1985

Related U.S. Application Data

[62] Division of Ser. No. 608,005, May 7, 1984, Pat. No. 4,576,747.

[51] Int. Cl.[4] .................. C07D 205/08; C07D 403/14; C07D 403/12
[52] U.S. Cl. .................................................... 540/356
[58] Field of Search .................................... 260/239 A

[56] References Cited

U.S. PATENT DOCUMENTS 3,265,684 8/1966 Herweh et al. ................. 260/239 A

OTHER PUBLICATIONS

Ebnöther et al., *Helvetica Chemica Acta*, 42, 1959, pp. 918 to 955.
James C. Martin et al., *J. Org. Chem.*, 36, 1971, pp. 2205 to 2210.

*Primary Examiner*—Mark L. Berch
*Attorney, Agent, or Firm*—James S. Rose

[57] ABSTRACT

Novel isocyanato-azetidinedione compounds are provided which have the formula

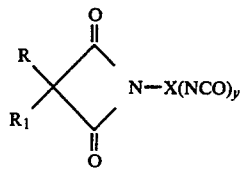

wherein R and $R_1$ can be independently selected from hydrogen and hydrocarbyl or can be joined together and along with the carbon to which they are attached represent a cycloalkane residue having 4 to 6 ring carbon atoms, y is an integer from 1 to 7 and X is a hydrocarbon radical having a valency of y plus one.

The monoisocyanate compounds are used as intermediates to provide further novel azetidinedione containing derivatives in the form of azetidinedione-isocyanurates (II) and azetidinedione-urethanes (III).

All three classes of compounds can be employed as acid scavenging agents for stabilizing various kinds of halogenated polymer systems. Notably, (I) and (III) form highly useful polyamide-polyureas and polyamide-polyurethanes respectively by reaction with organic polyamines.

8 Claims, No Drawings

AZETIDINEDIONE URETHANES

CROSS-REFERENCE TO RELATED APPLICATION

This is a divisional of application Ser. No. 608,005 filed May 7, 1984, now U.S. Pat. No. 4,576,747.

BACKGROUND OF THE INVENTION

1. Field of the Invention

This invention relates to azetidinediones and is more particularly concerned with novel isocyanato-azetidinediones and particular azetidinedione-isocyanurates and azetidinedione-urethanes prepared from said isocyanatoazetidinediones.

2. Description of the Prior Art

Various azetidine-2,4-dione compounds have been described in the art; for typical disclosures of such compounds see U.S. Pat. No. 3,265,684, Ebnöther et al, Helvetica Chemica Acta, 42, 1959, pp 918 to 955, and Martin et al, J. of Organic Chemistry, 36, 1971, pp 2205 to 2210.

I have now discovered what I believe to be a novel class of isocyanato-azetidinediones defined below. These compounds possess a degree of stability in the azetidinedione ring which allows for their conversion to other azetidinedione ring containing compounds without the opening of the ring or polymerization thereof. Such stability would not have been predictable from the prior art.

SUMMARY OF THE INVENTION

This invention comprises isocyanato-azetidinediones having the formula (I)

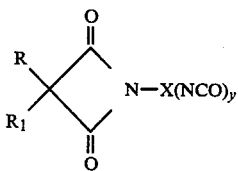

I wherein R and $R_1$ when taken individually are independently selected from the group consisting of hydrogen and hydrocarbyl, and R and $R_1$, when taken together with the carbon atom to which they are attached, represent a cycloalkane residue having 4 to 6 ring carbon atoms, inclusive, y is an integer from 1 to 7, and X is a hydrocarbon radical having a valency of y plus one.

The invention also comprises azetidine-dioneisocyanurates having the formula (II) and azetidinedioneurethanes having the formula (III)

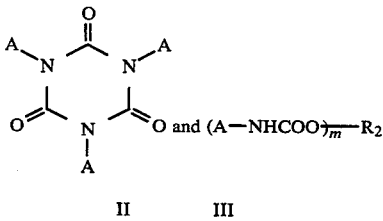

II  III wherein each A represents the group

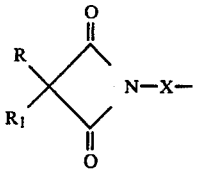

wherein R and $R_1$ have the same significance as set forth above, $R_2$ is the residue of a hydroxyl compound containing m hydroxyl groups wherein the value of m is from about 1 to about 8, and X is the divalent form of the hydrocarbon radical X defined above.

The term "hydrocarbyl" means the monovalent radical obtained by removing one hydrogen atom from the parent hydrocarbon having from 1 to 18 carbon atoms. Illustrative of hydrocarbyl are alkyl such as methyl, ethyl, propyl, butyl, pentyl, hexyl, octyl, decyl, dodecyl, hexadecyl, octadecyl, and the like, including isomeric forms thereof; alkenyl such as vinyl, allyl, butenyl, pentenyl, hexenyl, octenyl, decenyl, undecenyl, tridecenyl, hexadecenyl, octadecenyl, and the like, including isomeric forms thereof; aralkyl such as benzyl, phenylethyl, phenylpropyl, benzhydryl, naphthylmethyl, and the like; aryl such as phenyl, tolyl, xylyl, naphthyl, biphenylyl, and the like; cycloalkyl such as cyclobutyl, cyclopentyl, cyclohexyl, cycloheptyl, cyclooctyl, and the like including isomeric forms thereof; and cycloalkenyl such as cyclopentenyl, cyclohexenyl, cycloheptenyl, cyclooctenyl, and the like, including isomeric forms thereof.

The hydrocarbyl groups which form the groups R and $R_1$ can be substituted by one or a plurality of substituents provided the latter are not reactive with the azetidinedione ring common to formulae (I), (II), and (III), the isocyanate groups of (I), the isocyanurate ring of (II), and urethane linkages of (III). Illustrative of such substituents are halo, i.e. chloro, bromo, fluoro, and iodo; nitro; alkoxy from 1 to 8 carbon atoms, inclusive, such as methoxy, ethoxy, propoxy, butoxy, pentyloxy, hexyloxy, heptyloxy, octyloxy, and the like, including isomeric forms thereof; alkylmercapto from 1 to 8 carbon atoms, inclusive, such as methylmercapto, ethylmercapto, propylmercapto, butylmercapto, pentylmercapto, hexylmercapto, heptylmercapto, octylmercapto, and the like, including isomeric forms thereof; and cyano.

The term "cycloalkane having 4 to 6 ring carbon atoms" is inclusive of cyclobutane, 3-methylcyclobutane, cyclopentane, 3-methylcyclopentane, cyclohexane, 3-methylcyclohexane, 4-methylcyclohexane, and the like.

The term "hydrocarbon radical having a valency of y plus one" means the divalent, trivalent, tetravalent, pentavalent, hexavalent, heptavalent, and octavalent radical obtained by removing two, three, four, five, six, seven or eight hydrogen atoms from the parent hydrocarbon having a carbon atom content of from 2 to 36, inclusive, such as alkylene, cycloalkylene, arylene, divalent radicals having the formula

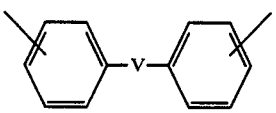

wherein V is selected from the group consisting of —CO—, —O—, —SO$_2$—, and alkylene having 1 to 4 carbon atoms, inclusive, and polymethylene polyphenylene radicals having the formula

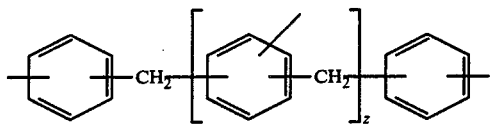

wherein z is 0 or a number having an average value from 0 to 1.

DETAILED DESCRIPTION OF THE INVENTION

Isocyanato-Azetidinediones (I)

The novel isocyanato-azetidinediones in accordance with the present invention are defined by the formula (I) above. They exhibit good solubility in the common organic solvents such as ethers, for example, dibutyl ether, dioxane, and the like; esters, for example, ethyl acetate, butyl acetate, and the like; ketones, for example, acetone, methylethyl ketone, and the like; chlorinated solvents, for example, chloroform, carbon tetrachloride, and the like; aromatic solvents, for example, benzene, toluene, xylene, and the like; and dipolar aprotic solvents, for example, acetonitrile, dimethylacetamide, and the like. They are generally less soluble in the low molecular weight aliphatic and cycloaliphatic hydrocarbons (pentane, hexane, cyclohexane, and the like).

The compounds (I) are further characterized by strong absorption in the infrared at from about 1710 cm$^{-1}$ to about 1745 cm$^{-1}$ and weaker absorption at 1859 cm$^{-1}$ due to the carbonyl groups at the 2 and 4 positions of the azetidinedione ring, and by strong absorption at about 2275 cm$^{-1}$ due to the isocyanate group(s).

Illustrative but not limiting of the isocyanatoazetidinediones (I) in accordance with the present invention are N-(6-isocyanatohexyl)azetidine-2,4-dione, N-(6-isocyanatohexyl)-3,3-dimethylazetidine-2,4-dione, N-(6-isocyanatohexyl)-3,3-diethylazetidine-2,4-dione, N-(6-isocyanatohexyl)-3-ethyl-3-butylazetidine-2,4-dione, N-(6-isocyanatohexyl)-3-methyl-3-allylazetidine-2,4-dione, N-(6-isocyanatohexyl)-3-benzylazetidine-2,4-dione, N-(6-isocyanatohexyl)-3-phenylazetidine-2,4-dione, N-(6-isocyanatohexyl)-3,3-pentamethyleneazetidine-2,4-dione, N-(3-isocyanatocyclopentyl)-3,3-dimethylazetidine-2,4-dione, N-(4-isocyanatocyclohexyl)-3,3-dimethylazetidine-2,4-dione, N-(4-isocyanatocyclohexyl)-3-ethyl-3-butylazetidine-2,4-dione, N-(4-isocyanatophenyl)-3,3-dimethylazetidine-2,4-dione, N-(4-isocyanatophenyl)-3,3-dibutylazetidine-2,4-dione, N-(4-isocyanatophenyl)-3-ethyl-3-butylazetidine-2,4-dione, N-(3-isocyanato-4-methylphenyl)-3,3-dimethylazetidine-2,4-dione, N-(3-isocyanato-4-methylphenyl)-3,3-diethylazetidine-2,4dione, N-(3-isocyanato-4-methylphenyl)-3-ethyl-3-butyl-azetidine-2,4-dione, N-(3-isocyanato-6-methylphenyl)-3,3-dimethylazetidine-2,4-dione, N-(3-isocyanato-6-methyl-phenyl)-3-ethyl-3-butylazetidine-2,4-dione, N-(2-methyl-3-isocyanatophenyl)-3,3-dimethylazetidine-2,4-dione, N-(2-methyl-3-isocyanatophenyl)-3,3-diethylazetidine-2,4-dione, N-(2-methyl-3-isocyanatophenyl)-3-ethyl-3-butylazetidine-2,4-dione, 4-isocyanato-4'-(3,3-dimethyl-2,4-dioxo-azetidino)diphenylmethane, 4-isocyanato-4'-(3,3-diethyl-2,4-dioxo-azetidino)diphenylmethane, 4-isocyanato-4'-(3,3-dipropyl-2,4-dioxo-azetidino)diphenylmethane, 4-isocyanato-4'-(3-ethyl-3-butyl-2,4-dioxoazetidino)diphenylmethane, 4-isocyanato-4'-(3-benzyl-2,4-dioxo-azetidino)diphenylmethane, 4-isocyanato-4'-(3-phenyl-2,4-dioxo-azetidino)diphenylmethane, 4-isocyanato-4'-(3,3-pentamethylene-2,4-dioxo-azetidino)diphenylmethane, and the like; and the polyisocyanato-azetidinediones wherein the equivalent of about one isocyanate group in triphenylmethane-4,4',4''-triisocyanate, 1,6,11-undecane triisocyanate, or a polymethylene polyphenyl polyisocyanate having an equivalent weight of about 130 to about 160, is replaced by a 3,3-dimethyl-, 3,3-diethyl-, or 3-ethyl-3-butyl-2,4-dioxo-azetidino radical.

The isocyanato-azetidinediones are prepared by processes which are analogous to those known in the art. Illustratively, the compounds can be prepared using a procedure analogous to that set forth in U.S. Pat. No. 3,265,684, cited supra, according to the following equation:

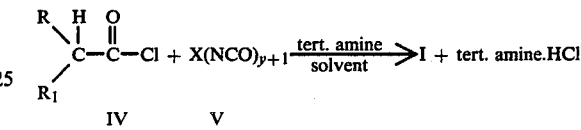

The acid chloride (bromide, iodide, or fluoride can also be used) starting materials (IV) are well known and readily available compounds wherein R and R$_1$ have the significance set forth above.

The isocyanate reactants (V) wherein X and y have the same significance as set forth above can be any of the known polyfunctional organic isocyanates A preferred group of the polyisocyanates which can be employed are hexamethylene diisocyanate; 1,4-cyclohexylene diisocyanate, methylenebis(cyclohexyl isocyanate), isophorone diisocyanate; methylenebis(phenyl isocyanate) including the 4,4'- and 2,4'-isomers and mixtures thereof, m- and p-phenylene diisocyanates, 2-chloro-p-phenylene diisocyanate, 2,4- and 2,6-toluene diisocyanate and mixtures thereof, 1,5-naphthalene diisocyanate, 1,6,11-undecane triisocyanate, triphenylmethahe-4,4',4''-triisocyanate, the liquefied forms of methylenebis(phenyl isocyanate) such as those described in U.S. Pat. No. 3,384,653; and the polymethylene polyphenyl polyisocyanates.

The proportions in which the acid halide (IV) and isocyanate (V) are reacted together are not critical but are preferably about equimolar, and, most preferably the isocyanate is employed in up to 100 percent mole excess over the acid halide concentration.

The reaction is carried out by heating the reactants together in an inert organic solvent at a temperature of at least about 75° C. in the presence of an acid halide acceptor, preferably, a tertiary organic amine such as triethyl amine, tributyl amine, pyridine, and the like. The term "inert organic solvent" means an organic solvent which does not interact with the reactants or the product or otherwise interfere with the reaction Illustrative of the solvents which can be employed are the solvents set forth above in which the products are soluble.

The progress and completion of the reaction can be easily monitored by conventional analytical procedures such as by infrared spectroscopy, nuclear magnetic resonance spectroscopy, and like analytical methods.

Generally speaking, the hydrohalide salt of the tertiary amine precipitates from solution and is readily removed by filtration. The solvent is removed by standard methods such as distillation either at atmospheric or reduced pressure to yield the product. The latter can be purified, if desired, by routine procedures such as distillation and/or recrystallization, chromatography and the like.

The compounds of formula (I) all possess the property of forming highly useful polyamide-polyurea copolymers when polymerized with organic polyamines. The isocyanate groups react with the amine function in the well known manner to form the urea linkages. The amide linkages are formed from the facile opening of the azetidinedione ring by the amine. Accordingly, typical copolymers are formed in accordance with the following representative schematic equation wherein the compound (I) is a monoisocyanate (Ia) and the polyamine is a diamine,

wherein B is the organic residue of the polyamine.

It will be understood by one skilled in the art that the above equation and recurring unit produced thereby are illustrative only of the linear types of polymers that can be prepared. When y in (I) is greater than 1 and/or the polyamine has a functionality greater than 2 then cross-linked polymers will result.

The polymerization process can be carried out using any prior art methods for reacting polyamines with polyisocyanates to prepare polyureas. For example, see U.S. Pat. Nos. 4,296,212; 4,374,210 and 4,433,067 for typical reactants and procedures and whose disclosures are herein incorporated by reference. The copolymers can be prepared in bulk, cast, or molded form depending on the end-use desired, the presence or absence of other ingredients, and the like.

Generally speaking, the compound (I) and the polyamine are polymerized in substantially equivalent amounts wherein the term "equivalent" in reference to both reactants refers to their molecular weights divided by their respective functionalities. The term "functionality" in reference to the polyamines is simply the number of amine groups whereas in reference to (I) the azetidinedione ring serves as one functional group while the isocyanate(s) serves as the other funtional group(s).

Illustratively, the organic polyamines can have an amine functionality of from 2 to 6 and a molecular weight of from about 60 to about 5000; such as ethylene diamine, butylene diamine, amine terminated polyether polyols having 2 or 3 primary or secondary amine groups and a molecular weight of from about 1000 to about 4000.

Most useful of the polyamide-polyurea copolymers are the linear ones prepared from the difunctional compounds (Ia) and the organic diamines.

The polyamide-polyurea copolymers can be rapidly molded to form auto parts such as bumpers, body elements, panels, doors, engine hoods, skirts, air-scoops, and the like.

Also the compounds (I) in accordance with the present invention are useful as acid and water scavenging agents for stabilizing various kinds of halogenated polymer systems such as chlorinated polymers and particularly polyvinyl chloride. The monoisocyanates (Ia) are particularly useful for the preparation of the novel azetidinedione-isocyanurates (II) and azetidine-dione-urethanes (III) discussed below.

Azetidinedione-isocyanurates (II)

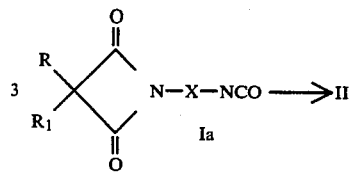

The novel azetidinedione-isocyanurates (II) in accordance with the present invention are obtained via the trimerization of the monoisocyanato-azetidinediones (Ia) as set forth in the above reaction scheme wherein X, R, and $R_1$ are defined above.

The azetidinedione-isocyanurate compounds can be used as acid scavenging agents for stabilizing the same types of halogenated polymer systems referred to above.

The preferred class of monoisocyanates (Ia) for the trimerization to (II) is the one wherein X is a divalent hydrocarbon radical, and, particularly, an arylene radical or a radical having the formula

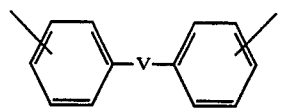

defined above and R and $R_1$ are the same or different alkyl groups.

Illustrative but not limiting of the monoisocyanates which are readily trimerized to the isocyanurates (II) are the monoisocyanate-azetidinediones exemplified above.

Preferred species for the trimerization to (II) are those monoisocyanates exemplified above wherein X is 4-methylphenylene, 6-methylphenylene, and mixtures thereof, and 4,4'-methylenebisphenylene.

The trimerization process is carried out using any of the methods and techniques well known to those skilled in the art; for illustrative methods see Saunders and Frisch, Polyurethanes Chemistry and Technology, Part I, 1962, pp 94 to 95, Interscience Publishers, New York, N.Y., and U.S. Pat. Nos. 2,979,485; 2,993,870 and 3,381,008 whose patent disclosures are incorporated herein by reference.

The trimerization is preferably carried out in the presence of an inert solvent, i.e. a solvent that does not react with isocyanate groups or otherwise interfere with the course of the trimerization. Preferred solvents are aromatic solvents such as benzene, toluene, xylene, nitrobenzene, chlorobenzene and the like, and aliphatic esters such as ethyl acetate, butyl acetate, and the like.

Advantageously, the trimerization is carried out at a temperature falling within a range of about 50° C. to about 200° C., preferably about 75° C. to about 150° C. and in the presence of a trimerization catalyst.

Any of the catalysts known in the art for the trimerization of isocyanates may be employed. Typical are those disclosed in the following: The Journal of Cellular Plastics, November/December 1975, p 329; U.S. Pat.

Nos. 3,745,133; 3,896,052; 3,899,443; 3,903,018; 3,954,684 and 4,126,742, and mixtures of any of the catalysts disclosed therein. The disclosures of these patent references are incorporated herein by reference.

A preferred group of catalysts comprises the alkali metal salts of lower alkanoic acids such as the sodium, potassium, or lithium salts of formic acid, acetic acid, propionic acid, butyric acid, heptanoic acid, 2-methylhexanoic acid, 2-ethylhexanoic acid, and the like.

The catalyst concentration is not critical, and, advantageously, falls within a range of from about 0.1 part to about 10 parts by weight per equivalent of isocyanate.

Surprisingly, the azetidinedione ring remains stable under the conditions of the trimerization process which includes high temperatures (as high as 170° C.) while in the presence of the strongly basic trimerization catalysts. This is highly unexpected as the azetidinedione ring is known to open readily under basic conditions. Also, the closely related β-lactams (azetidinones) readily ring-open and polymerize under mild basic conditions because of the steric strain in a 4-membered ring. Certain trimerization catalysts, such as the very strongly basic ones like potassium tertiary butoxide and sodium methoxide, do tend to cause some ring decomposition during trimerization. However, the majority of the trimerization catalysts provide the desired products.

Generally speaking, the isocyanurate products are solids and are easily isolated from their reaction solutions by removing the solvent using known methods.

Azetidinedione-urethanes (III)

The novel azetidine-urethanes (III) in accordance with the present invention are obtained via the reaction of the monoisocyanato-azetidinediones (Ia) defined above with the hydroxyl compounds defined by the formula $R_2(OH)_m$ as shown in the equation set forth above and using the appropriate stoichiometric proportions of the isocyanate to react with substantially all of the hydroxyl functionality. Any of the well known procedures in the art for reacting isocyanate compounds with hydroxyl containing compounds to form urethanes and polyurethanes, either with or without solvent, can be employed in preparing the compounds (III) in accordance with the present invention. For detailed methods and illustrative techniques for urethane preparation see Saunders and Frisch, Polyurethanes Chemistry and Technology, Part I cited supra and also Part II of the same series.

The hydroxyl compounds which can be employed include any of the primary and secondary hydroxyl containing compounds having a MW from about 32 to about 5000 such as the aliphatic, aromatic and cycloaliphatic mono-alcohols and organic polyols having a functionality of from 2 to 8. Typical mono-alcohols but not limiting thereof are methanol, ethanol, butanol, phenol, cyclohexanol, and the like.

Of the organic polyols the functionality is preferably from 2 to 3, and most preferably 2. A preferred molecular weight range is from about 60 to about 3000.

A preferred class of polyhydric alcohols are the low molecular weight alkylene glycols, i.e., ethylene glycol, 1,4-butanediol, 1,5-pentanediol, 1,6-hexanediol, diethylene glycol, and the like; and the polyalkyleneoxy glycols of MW range of about 200 to about 2000 such as polyethyleneoxy glycols, polypropyleneoxy glycols, polyethyleneoxy-polypropyleneoxy glycols, and polytetramethyleneoxy glycols.

Surprisingly, even at elevated reaction temperatures and in the presence of urethane catalysts, the azetidinedione ring remains stable to the hydroxyl groups of the polyol component and does not polymerize with them.

The products are characterized by strong infrared absorption at about 1740 cm$^{-1}$ and weaker absorptions at 1850 cm$^{-1}$ due to the azetidinedione rings.

The urethane products range from viscous liquids to solids (both crystalline and amorphous) depending largely on the molecular weight and functionality of the polyol employed. If the preparation is carried out in the absence of solvent the product can be obtained directly. Otherwise the products are easily isolated from their reaction solutions using known methods.

The compounds of formula (III) wherein m is greater than one, similarly to those of (I) discussed above, react readily with organic polyamines, and, in this case, to form highly useful polyamide-polyurethane copolymers. Again, for ease of illustration only, the following schematic equation sets forth the linear copolymer recurring unit obtained from the polymerization of a compound (III) wherein m=2 with an organic diamine.

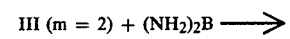

The polyamine has the same significance discussed above and the same preparative procedures and teaching referred to above for the polyamide-polyureas applies to the preparation of the polyamide-polyurethanes. In respect of the equivalent weight of the compound (III) it refers to the molecular weight of the compound divided by its number of azetidinedione rings which latter represent functional groups.

Most useful of the polyamide-polyurethanes are the linear ones.

The polyamide-polyurethanes can be molded to form the same types of auto parts described above for the polyamide-polyureas.

The compounds (III) wherein m equals one are useful as acid scavenging agents for the stabilization of halogenated polymers.

The following examples describe the manner and process of making and using the ivention and set forth the best mode contemplated by the inventor of carrying out the invention but are not to be construed as limiting.

EXAMPLE 1

A 2 liter three-necked reaction flask equipped with a stirrer, reflux condenser, thermometer, addition funnel, and gas inlet tube was charged with a solution of 105 g. (0.6 mole) of 2,4-toluene diisocyanate and 45 g. (0.42 mole) of isobutyryl chloride dissolved in 500 ml. of xylene. The solution was stirred and heated in an oil bath to a temperature of 115° to 120° C.

A solution of 65 g. (0.64 mole) of triethylamine dissolved in 50 ml. of xylene was added dropwise to the reaction solution through the addition funnel and under a nitrogen atmosphere over a 4 hour period. Heating of the stirred solution was continued for a further 3 hour period. The solution was cooled to about 0° C. and the precipitated solid of triethylamine hydrochloride was separated by filtration. The filter cake was washed with fresh xylene and these washings added to the filtrate.

The filtrate and washings were distilled to remove the solvent using a rotary evaporator under a pressure of about 15 mm. of mercury and a temperature of about 70° C. An oily residue was obtained. The oil was vacuum distilled using a short Vigreux column under a pressure of 0.08 mm. of mercury. The first fraction, b.p.=60°-120° C., wt.=41.4 g., was a 39 percent recovery of starting 2,4-toluene diisocyanate; the second fraction, b.p.=120°-145° C., wt.=63.1 g. solidified on standing, m.p.=58° to 70° C. Recrystallization of the latter product from 50 ml. of cyclohexane provided 44.2 g. of crystalline solid, m.p.=71°-80° C. representing a 45 percent yield of an isocyanato-azetidinedione mixture of the two isomeric compounds (a) N-(3-isocyanato-4-methylphenyl)-3,3-dimethylazetidine-2,4-dione and (b) N-(3-isocyanato-6-methylphenyl)-3,3-dimethylazetidine-2,4-dione in accordance with the present invention and having the formulae

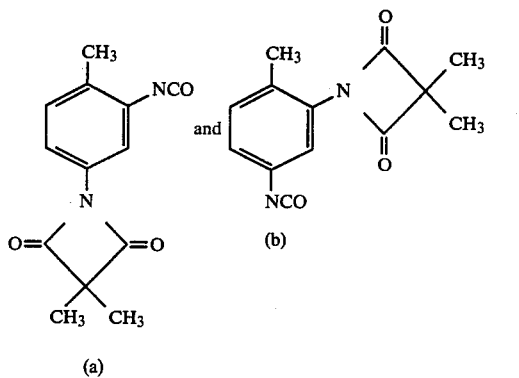

The NMR integration showed that the proportion of isomer (a) to isomer (b) in the reaction product was 60/40 respectively. The isomer (a) was separated by repeated recrystallization from cyclohexane with (a) having the higher m.p.=89° C.

Elemental analysis for isomer (a): Calculated for $C_{13}H_{12}N_2O_3$: C=63.93%, H=4.95%, N=11.47%; Found: C=63.84%, H=5.08%, N=11.31%.

Infrared for mixture of (a) and (b) ($CCl_4$) (in $cm^{-1}$): 2960, 2910, 2275(s), 1859, 1741(s), 1605, 1512, 1390(s), 1375, and 1040.

Proton nuclear magnetic resonance for isomer (a) ($CDCl_3$): $\delta$ 6 7.52 (multiplet, 2 protons), 7.00-7.28 (m,1) 7.34 (singlet,3), 2.36 (s, 3), 1.50 and 1.45 (s,6).

EXAMPLE 2

Using a similar procedure and apparatus as described in Example 1 except on a smaller scale, a stirred solution of 17.5 g. (0.1 mole) of 2,4-toluene diisocyanate and 20.0 g. (0.15 mole) of α-ethylbutyryl chloride dissolved in 125 ml. of xylene was heated to about 120° C.

Over a 6 hour period a solution of 21 g. (0.21 mole) of triethylamine dissolved in 10 ml. of xylene was added to the stirred solution at the above temperature. The solution was stirred and heated at 140° C. overnight (about 15 hours). The cooled solution (about 0° C.) was filtered to remove the solid triethylamine hydrochloride which was washed with fresh xylene and the washings added to the filtrate.

The solvent was removed from the combined filtrate and washings in a rotary evaporator at about 15 mm. of mercury pressure and a temperature of 70° C. An oily residue of wt.=34.3 g. remained. It was vacuum distilled using the apparatus described in Example 1 and under a pressure of 0.05 mm. of mercury. The first fraction, b.p.=65° to 70° C., wt.=3.2 g. was an 18 percent recovery of the starting 2,4-toluene diisocyanate. The second fraction had a b.p.=145°-150° C., (wt.=9.5 g.) and was recovered as an oil representing a 35 percent yield of an isocyanato-azetidinedione mixture of the two isomers (a) N-(3-isocyanato-4-methylphenyl)-3,3-diethyl-azetidine-2,4-dione and (b) N-(3-isocyanato-6-methyl-phenyl)-3,3-diethylazetidine-2,4-dione in accordance with the present invention and having the formulae

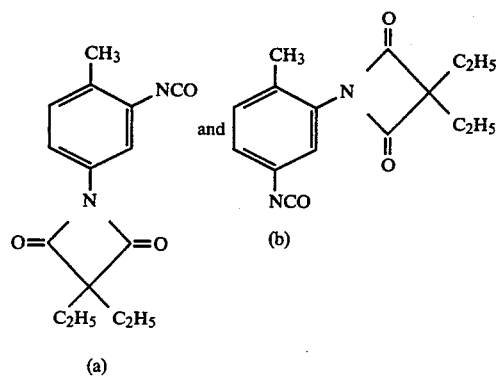

Infrared for the mixture (Neat) (in $cm^{-1}$): 2952, 2915, 2860, 2255(s), 1861, 1840, 1735(s), 1600, 1570, 1510, 1455, 1380, 1040.

Proton NMR for the mixture ($CDCl_3$): $\delta$ 7.65 (m,1), 7.40-7.18 (m,2), 2.40 (s,3), 1.86 (m,4), 1.13 (m,6).

The relative proportions of (a) to (b) in the mixture could not be determined with the same precision as in the previous Example 1 because of the more complex resonance of the ethyl groups. However, isomer (a) was assumed to be in excess because of lower steric hindrance in (a) as opposed to (b).

EXAMPLE 3

Using a similar procedure and apparatus as described in Example 1, a stirred solution of 52.0 g. (0.3 mole) of 2,4-toluene diisocyanate and 25 g. (0.15 mole) of 2-ethylhexanoyl chloride dissolved in 450 ml. of xylene was heated to 138° to 145° C.

Over a period of 4 to 5 hours a solution of 30.0 g. (0.3 mole) of triethylamine dissolved in 20 ml. of xylene was added to the stirred solution at the above temperature. The solution was stirred and heated within the above temperature range for an additional 2 hour period. The solution was cooled to about 0° C. and the precipitated triethylamine hydrochloride was removed by filtration. The precipitate was washed with fresh xylene which was added to the filtrate.

The solvent was removed from the combined filtrate and washings in a rotary evaporator at about 15 mm. of mercury pressure and a temperature of 70° C. An oily residue, wt.=84.1 g. was obtained. The residue was distilled using the apparatus described in Example 1 and under a pressure of 0.1 mm. of mercury. The first fraction, b.p.=60° to 110° C., wt.=32.7 g. was a 63 percent recovery of the starting 2,4-toluene diisocyanate. The second fraction, b.p.=130 to 160° C., wt.=34.2 g., was isolated as an oil and represented a 76 percent yield of an isocyanato-azetidinedione mixture of the two isomers (a) N-(3-isocyanato-4-methylphenyl)-3-ethyl-3-butylazetidine-2,4-dione and (b) N-(3-isocyanato-6-methylphenyl)-3-ethyl-3-butylazetidine-2,4-dione in accordance with the present invention and having the formulae

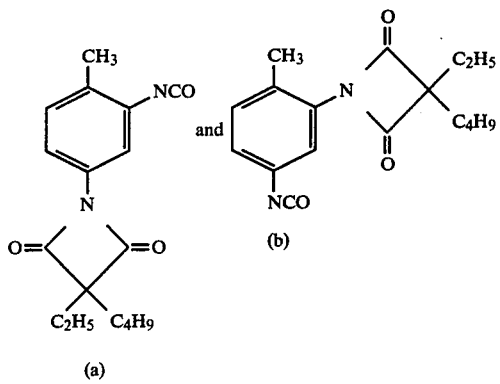

Infrared for the mixture (CCl₄) (in cm⁻¹): 2960, 2940, 2865, 2275(s), 1862, 1740(s), 1613, 1580, 1520, 1460, 1382.

Proton NMR for the mixture (CDCl₃): δ 7.60 (m,l), 6.90–7.20 (m,2), 2.38(s,3), δ 2.10–0.90 (m,14).

Elemental analysis for the mixture: Calculated for $C_{17}H_{20}N_2O_3$: C=67.98%, H=6.71%, N=9.33%; Found: C=68.02%, H=6.54%, N=9.42%. Similarly to Example 2 above, the relative proportions of (a) to (b) in the mixture could not be determined with precision but isomer (a) was assumed to be the major component.

EXAMPLE 4

Using a similar procedure and apparatus as described in the previous examples, a stirred solution of 50 g. (0.2 mole) of 4,4'-methylenebis(phenyl isocyanate) and 16 g. (0.15 mole) of isobutyryl chloride dissolved in 250 ml. of xylene was heated to about 120° C.

Over a 3 hour period a solution of 25 g. (0.25 mole) of triethylamine dissolved in 20 ml. of xylene was added to the stirred solution at the above temperature. The heating and stirring was continued for a further 3 hour period. The solution was cooled to about 0° C. and the solid triethylamine hydrochloride was removed by filtration and washed with fresh xylene which latter was added to the filtrate The solvent was removed from the combined filtrate and washings in a rotary evaporator at about 15 mm. of mercury pressure and a temperature of 70° C. A solid residue was obtained, wt.=55.1 g. This residue was recrystallized from 80 ml. of cyclohexane to provide 13.3 g. of crystalline solid, m.p.=100° C. representing a 27 percent yield of 4-isocyanato-4'-(3,3-dimethyl-2,4-dioxo-azetidino)diphenylmethane in accordance with the present invention and having the formula

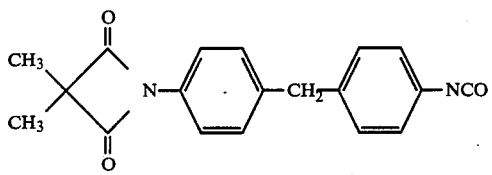

Elemental analysis: Calculated for $C_{19}H_{16}N_2O_3$: C=71.24%, H=5.02%, N=8.74%; Found: C=71.76%, H=4.67%, N=8.87%.

Infrared (CCl₄) (in cm⁻¹): 2955, 2910, 2255(s), 1852, 1743(s), 1601, 1512(s), 1390, 1368.

Proton NMR (CDCl₃): δ 7.71 (d,2), 7.14 (d,2), 7.02 (s,4), 3.93 (s,2), 1.46 (s,6).

EXAMPLE 5

Using a similar procedure and apparatus as described in the previous examples a stirred solution of 20 g. (0.12 mole) of hexamethylene diisocyanate and 30 g. (0.28 mole) of isobutyryl chloride dissolved in 150 ml. of xylene was heated to about 120° C.

Over an 8 hour period a solution of 35 g. (0.34 mole) of triethylamine dissolved in 30 ml. of xylene was added to the stirred solution at the above temperature. The heating and stirring was continued overnight (about 16 hours). After about 24 hours of heating, the reaction solution was cooled to about 0° C. and the precipitated triethylamine hydrochloride was removed by filtration and washed with fresh xylene which was combined with the filtrate.

The solvent was removed from the combined filtrate and washings in a rotary evaporator at about 15 mm. of mercury pressure and a temperature of 80° C. A residue of an oil remained which was vacuum distilled using the apparatus described in Example 1 and under a pressure of 0.1 mm. of mercury. A fore-fraction had a b.p.=50°–85° C. The main fraction had a b.p.=115°–120° C. and wt.=6.5 g. and remained a liquid representing a 22 percent yield of N-(6-isocyanatohexyl)-3,3-dimethylazetidine-2,4-dione in accordance with the present invention and having the formula

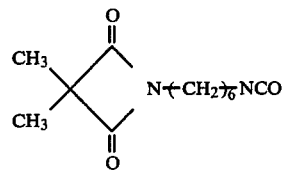

Infrared (Neat) (in cm⁻¹): 2920, 2850, 2255(s), 1721(s), 1450, 1435, 1390, 1350, 1250.

Proton NMR (CDCl₃): δ 3.32 (4,t), 2.0–1.0 (8,m), 1.38 (6,s).

EXAMPLE 6

Using a similar procedure and apparatus as described in the previous examples, a stirred solution consisting of 14.5 g. (0.106 eq.) of a polymethylene polyphenyl polyisocyanate mixture (isocyanate equiv.=137) containing about 40 to 45 percent by weight of methylenebis(phenyl isocyanate) and the remainder of said mixture consisting of polymethylene polyphenyl polyisocyanates having a functionality greater than 2, and 8.2 g. (0.05 mole) of 2-ethylhexanoyl chloride dissolved in 100 ml. of xylene was stirred and heated to 140° C.

Over a 2.5 hour period a solution of 7.5 g. (0.075 mole) of triethylamine dissolved in 20 ml. of xylene was added to the stirred solution at the above temperature. Stirring of the solution at 140° C. was continued for another 6 hours during which time the progress of the reaction was followed by infrared analysis on aliquot samples. The characteristic acid chloride absorption at 1785 cm⁻¹ disappeared and the two characteristic absorptions at 1740 and 1845 cm$^{-1}$ due to the azetidine-2,4-dione ring increased during the reaction period.

The reaction solution was cooled to about 0° C. and the precipitated triethylamine hydrochloride was removed by filtration. The filtrate was heated in a rotary evaporator at about 10 mm. of mercury pressure followed by higher vacuum (about 0.15 mm.) to remove all the solvent. An oily residue, wt.=21.8 g. was obtained; infrared analysis showed the characteristic azetidinedione absorption at 1740 and 1845 cm-:; isocyanate equiv. wt.=294 (theor.=267). This residue represented a 97 percent yield of an isocyanato-azetidinedione in accordance with the present invention having the representative formula

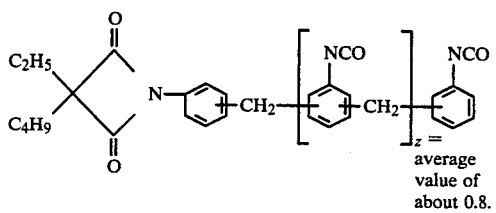

EXAMPLE 7

A 250 ml. reaction flask equipped with a magnetic stirrer, reflux condenser, and thermometer was charged with 25.0 g. (0.10 mole) of the isocyanato-azetidinedione mixture prepared in accordance with Example 1 above, 0.15 g. of a trimerization catalyst comprising about 67 percent by weight of potassium 2-ethylhexanoate dissolved in a polypropylene glycol of about 400 MW, and 32 ml. of ethyl acetate.

The solution was stirred and heated under reflux (reaction temperature of about 80° C.). Aliquot samples were removed periodically for infrared spectrum analysis to determine the progress of the trimerization of the isocyanate groups, i.e. their disappearance. After 12 hours the reaction was terminated as the isocyanate was totally consumed.

The reaction solution was poured into 150 ml. of ethyl acetate and washed with water in a separatory funnel to remove the catalyst from the product which latter remained in the organic solution. The organic layer was dried by storage over magnesium sulfate. The solution was filtered to remove the magnesium sulfate and was then heated in a rotary evaporator under about 15 mm. of mercury pressure to remove the ethyl acetate. The residue was a yellow colored resinous fluid when warm and which was dried further under 10 mm. of mercury pressure and 60° C. The product solidified to an amber colored resinous solid which was pulverized to pale yellow powder, wt.=24.5 g., melted at 200° to 260° C. representing a 98 percent yield of an azetidinedione-isocyanurate mixture in accordance with the present invention and represented by the formula

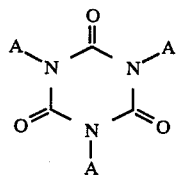

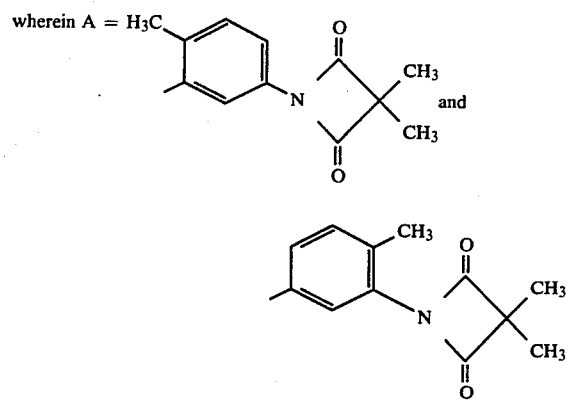

and mixtures of these groups in the same molecule.

Elemental analysis: Calculated for $C_{39}H_{36}N_6O_9$: C=63.93%, H=4.95%, N=11.47%; Found: C=63.58%, H=5.38%, N=11.17%.

Infrared (CCl$_4$) (in cm$^{-1}$): 3015, 2975, 2930, 2865, 1860, 1745(s), 1718(s), 1511, 1405, 1140, 1050.

When the same reactants as above but in smaller proportions (4.8 g. of the isocyanato-azetidinedione and 0.12 g. of the trimerization catalyst mixture) were reacted in 10 ml. of xylene at a temperature of about 120° C. the reaction was completed in 4 hours. The same solid resinous product was obtained.

EXAMPLE 8

Using the same apparatus and procedure set forth in Example 7 above, a 5.0 g. sample (0.02 mole) of the isocyanato-azetidinedione mixture prepared in accordance with Example 3 above was stirred and heated under reflux with 0.12 g. of the same trimerization catalyst used in Example 7 in 15 ml. of ethyl acetate.

After 18 hours the trimerization was complete as no more isocyanate absorption could be observed by infrared analysis. The solution was diluted to 50 ml. of ethyl acetate and washed with three separate portions of water in a separatory funnel. The organic layer was separated and dried over magnesium sulfate. After separating the drying agent the solution was stripped of solvent in a rotary evaporator under 10 mm. of mercury pressure. The residue was a resinous yellow solid which was easily pulverized (wt.=4.92 g.) and melted at 145° to 160° C. representing a 98 percent yield of an azetidinedioneisocyanurate mixture in accordance with the present invention and represented by the formula

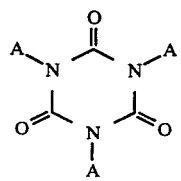

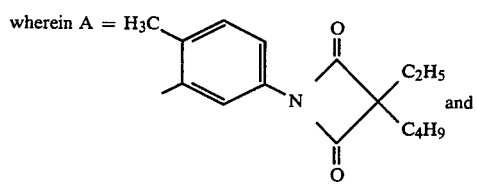

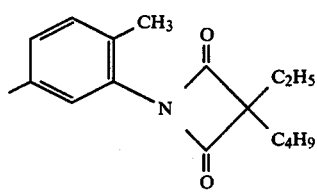

and mixtures of these groups in the same molecule.

Infrared (CHCl₃) (in cm¹): 3020, 2965, 2945, 2875, 1860, 1742(s), 1720(s), 1511, 1417(s), 1220, 1050.

EXAMPLE 9

The following experiment describes the preparation of a bis-urethane in accordance with the present invention.

A 100 ml. reaction flask equipped with a magnetic stirrer, condenser, and thermometer was charged with 5.0 g. (0.02 mole) of an isocyanato-azetidinedione mixture prepared in accordance with Example 1 above, 20.25 g. (0.01 mole) of a polyoxypropylene glycol having a molecular weight of about 2025, and about 0.035 g. of dibutyl tin dilaurate (0.2 drop).

The mixture was heated at 90 to 95° C. for about 18 hours and resulted in a cloudy viscous liquid. Infrared analysis showed that all of the isocyanate was consumed and the absorptions at 1850 and 1740 cm⁻¹ due to the azetidinedione ring remained intact. Gel permeation chromatography (GPC) in tetrahydrofuran solvent showed a single peak constituting greater than 95 percent by weight of the product mixture. Thus there was obtained a bis-urethane having the representative formula

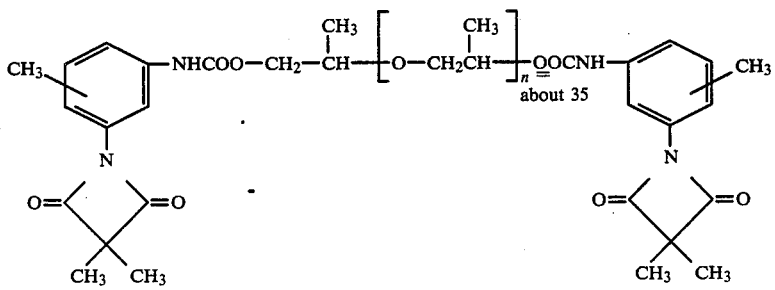

Using the same procedure and apparatus described above, 6.0 (0.02 mole) of an isocyanato-azetidinedione mixture prepared in accordance with Example 3 above, 20.23 g. (0.01 mole) of the same polyoxypropylene glycol as above, and 0.12 g. of dibutyl tin dilaurate were heated at 95°-100° C. for about 18 hours. Infrared analysis of the resulting clear viscous liquid showed complete consumption of isocyanate and the azetidinedione ring intact at 1860 and 1745 cm⁻: GPC analysis showed a single peak amounting to greater than percent by weight of the product mixture Thus there was obtained a bis urethane in accordance with the present invention having the formula

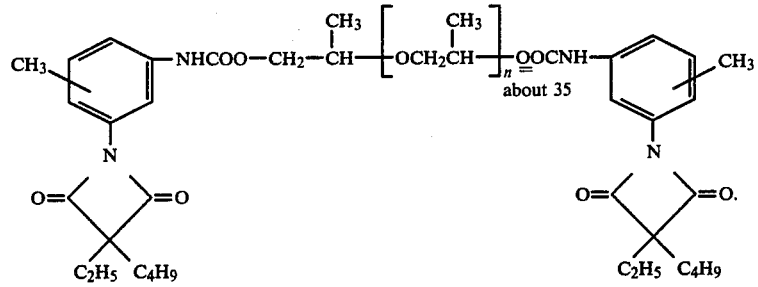

EXAMPLE 10

A 100 ml. reaction flask equipped similarly to the one described in Example 9 was charged with 0.45 g. (0.005 mole) of 1,4-butanediol, 5 g. (0.01 mole) of an isocyanato-azetidinedione mixture prepared in accordance with Example 1, 0.1 g. of dibutyl tin dilaurate, and ml. of ethyl acetate.

The mixture was stirred and heated at 80° to 90° C. for about 24 hours. Upon cooling a precipitate formed and was collected on a suction filter, washed with fresh ethyl acetate and thoroughly dried; wt.=1.45 g., m.p.=220° to 222° C.

Thus there was obtained a bis urethane in accordance with the present invention having the formula

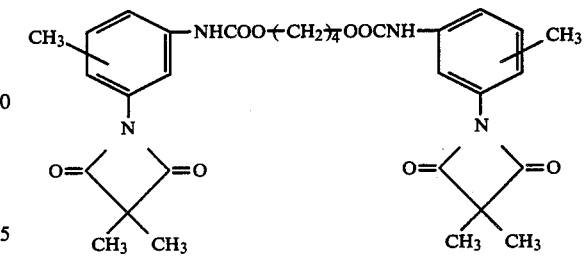

Infrared (CHCl₃) (in cm⁻¹) 3450, 3016, 2975, 1860, 1744, 1590, 1535, 1485, 1460, 1400, 1378, 1060.

Proton NMR (CDCl₃): δ 7.50-7.0 (m,6), 6.45 (s,2), 4.20 (t,4), 2.17 (s,6), 1.74 (t,4), 1.40 (s,12).

Elemental analysis: Calculated for $C_{30}H_{34}N_4O_8$: C=62.22%, H=5.92%, N=9.68%; Found: C=62.12%, H=6.12%, N=9.63%.

EXAMPLE 11

A 100 ml. reaction flask equipped according to Example 9 was charged with 0.90 g. (0.007 mole) of trimethylolpropane, 6.0 g. (0.02 mole) of an isocyanatoazetidinedione mixture prepared in accordance with Example 3 above, 0.1 g. of dibutyl tin dilaurate, and 10 ml. of ethyl acetate.

The mixture was stirred and heated at 80° to 90° C. for about 24 hours. No precipitate formed upon cooling the reaction solution The solvent was removed using a rotary evaporator under about 10 mm of mercury pressure to yield a resinous solid; m.p. greater than 70° C.

Thus there was obtained a tris urethane in accordance with the present invention having the formula

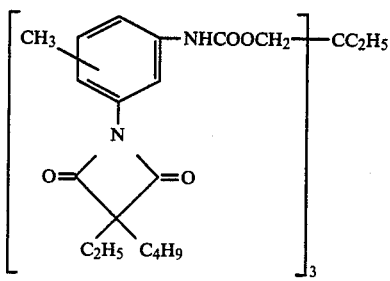

Infrared (CHCl$_3$) (in cm$^{-1}$): 3430, 3018, 2970, 2940, 2875, 1855, 1740(s), 1620, 1590, 1530, 1460, 1391.

Elemental analysis: Calculated for $C_{57}H_{74}N_6O_{12}$: C=66.13%, H=7.21%, N=12%, Found: C=66.04%, H=7.45%, N=8.09%.

I claim:

1. An azetidinedione urethane having the formula

wherein each A represents the group

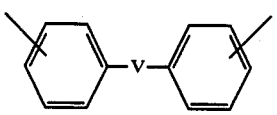

wherein R and R$_1$, when taken individually, are independently selected from the group consisting of hydrogen and hydrocarbyl having from 1 to 18 carbon atoms, and, when taken together with the carbon atom to which they are attached, represent a cycloalkane residue having 4 to 6 ring carbon atoms, inclusive, X is a divalent hydrocarbon radical having from 2 to 36 carbon atoms and divalent radicals having the formula

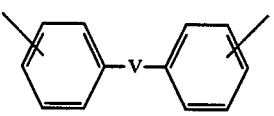

wherein V is selected from the group consisting of —CO—, —O—, —SO$_2$—, and alkylene having 1 to 4 carbon atoms, m has a value falling within the range of from about 1 to about 8, and R$_2$ is the residue of a primary or secondary hydroxyl compound having a molecular weight from about 32 to about 5000 and selected from the group consisting of aliphatic, aromatic, and cycloaliphatic mono-alcohols and polyols having a functionality of from 2 to 8.

2. An azetidinedione-urethane according to claim 1 wherein R and R$_1$ are the same or different alkyl.

3. An azetidinedione-urethane according to claim 1 wherein X is selected from the group consisting of arylene and divalent radicals having the formula

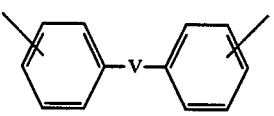

wherein V is selected from the group consisting of —CO—, —O—, —SO$_2$—, and alkylene having 1 to 4 carbon atoms, inclusive.

4. An azetidinedione-urethane according to claim 1 wherein m equals 2.

5. An azetidinedione-urethane according to claim 1 having the formula

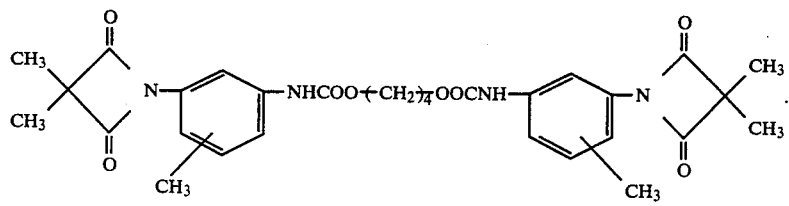

6. An azetidinedione-urethane according to claim 1 having the formula

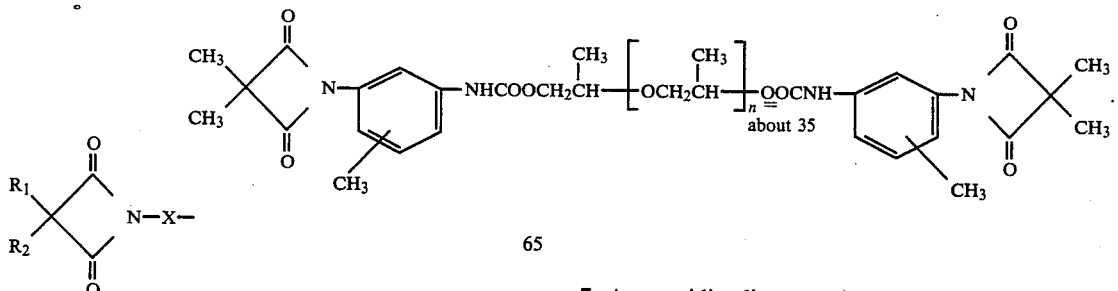

7. An azetidinedione-urethane according to claim 1 having the formula

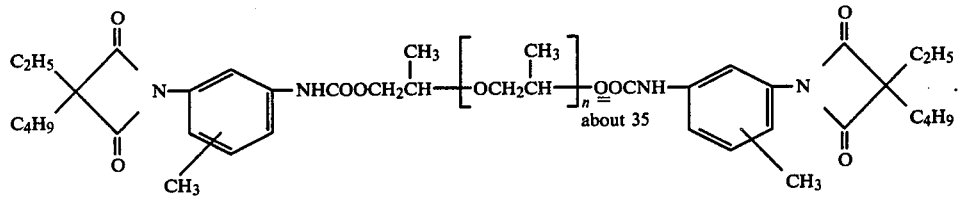
8. An azetidinedione-urethane according to claim 1 having the formula
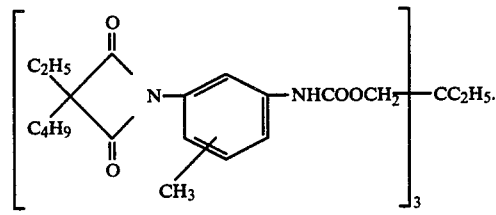

UNITED STATES PATENT AND TRADEMARK OFFICE
CERTIFICATE OF CORRECTION

PATENT NO. : 4,642,342

DATED : February 10, 1987

INVENTOR(S) : Shenghong A. Dai

It is certified that error appears in the above-identified patent and that said Letters Patent is hereby corrected as shown below:

Column 4, line 44 "triphenylmethahe-" should read -- triphenylmethane --. Column 8, line 31, that portion of the formula reading $$-CRR_1\overset{O}{\underset{\|}{C}}NHXHNH\overset{O}{\underset{\|}{C}}OR_2O\overset{O}{\underset{\|}{C}}NHXNH\overset{O}{\underset{\|}{C}}-$$ should read $$-CRR_1\overset{O}{\underset{\|}{C}}NHXNH\overset{O}{\underset{\|}{C}}OR_2O\overset{O}{\underset{\|}{C}}NHXNH\overset{O}{\underset{\|}{C}}-$$

Column 9, line 50 "(CDCl$_3$): δ 6 7.52" should read -- (CDCl$_3$): δ 7.52 --. Column 11, line 27 "(CDCl$_3$): 6 7.60" should read -- (CDCl$_3$): δ 7.60 --; line 31 the word "Similarly" should start a new paragraph. Column 13, line 11 "1845 cm :;" should read -- 1845 cm$^{-1}$; --. Column 15, line 67 the word "Infrared" should start a new paragraph. Column 16, line 2 "1745 cm :" should read -- 1745 cm$^{-1}$. --; line 3 "than percent" should read -- than 96 percent --. Column 17, line 32 "N = 12%" should read -- N = 8.12% --.

Signed and Sealed this

Eighteenth Day of August, 1987

Attest:

DONALD J. QUIGG

Attesting Officer

Commissioner of Patents and Trademarks